US011344653B2

(12) United States Patent
Arai et al.

(10) Patent No.: US 11,344,653 B2
(45) Date of Patent: May 31, 2022

(54) BONE FIXING MATERIAL

(71) Applicant: DAICEL CORPORATION, Osaka (JP)

(72) Inventors: Takashi Arai, Tokyo (JP); Yo Yamato, Himeji (JP); Koji Nakane, Fukui (JP); Naoki Shimada, Fukui (JP); Hanako Asai, Fukui (JP)

(73) Assignee: DAICEL CORPORATION, Osaka (JP)

( * ) Notice: Subject to any disclaimer, the term of this patent is extended or adjusted under 35 U.S.C. 154(b) by 132 days.

(21) Appl. No.: 16/472,604

(22) PCT Filed: Dec. 22, 2017

(86) PCT No.: PCT/JP2017/046243
§ 371 (c)(1),
(2) Date: Jun. 21, 2019

(87) PCT Pub. No.: WO2018/117266
PCT Pub. Date: Jun. 28, 2018

(65) Prior Publication Data
US 2020/0306414 A1 Oct. 1, 2020

(30) Foreign Application Priority Data

Dec. 22, 2016 (JP) .............................. JP2016-249366

(51) Int. Cl.
*A61L 27/58* (2006.01)
*A61L 27/18* (2006.01)
*A61L 27/56* (2006.01)
*C08L 71/10* (2006.01)

(52) U.S. Cl.
CPC .............. *A61L 27/58* (2013.01); *A61L 27/18* (2013.01); *A61L 27/56* (2013.01); *C08L 71/10* (2013.01); *A61L 2430/02* (2013.01); *C08L 2203/12* (2013.01)

(58) Field of Classification Search
None
See application file for complete search history.

(56) References Cited

U.S. PATENT DOCUMENTS

| 5,264,274 | A * | 11/1993 | Shigeta | B29C 43/12 442/212 |
| 5,478,470 | A | 12/1995 | Fukuda et al. | |
| 7,591,954 | B2 | 9/2009 | Kimura et al. | |
| 10,092,687 | B2 | 10/2018 | Kanaki et al. | |
| 2005/0038498 | A1 | 2/2005 | Dubrow et al. | |
| 2005/0129726 | A1 * | 6/2005 | Liebschner | C08L 67/04 424/423 |
| 2009/0162643 | A1 | 6/2009 | Dubrow et al. | |
| 2010/0215718 | A1 * | 8/2010 | Swords | A61L 27/227 424/423 |
| 2012/0177537 | A1 | 7/2012 | Aota et al. | |
| 2013/0256230 | A1 | 10/2013 | Dullaert et al. | |
| 2013/0277297 | A1 | 10/2013 | Suzuki et al. | |
| 2014/0272225 | A1 * | 9/2014 | Johnson | A61L 27/26 428/36.1 |
| 2014/0299556 | A1 | 10/2014 | Zambianchi et al. | |
| 2014/0358060 | A1 | 12/2014 | Laster | |
| 2015/0211160 | A1 * | 7/2015 | Hassan | D04H 3/16 428/141 |
| 2016/0129176 | A1 | 5/2016 | Kanaki et al. | |
| 2017/0165394 | A1 * | 6/2017 | Odermatt | A61L 15/64 |

FOREIGN PATENT DOCUMENTS

| JP | 4-64363 A | 2/1992 | |
| JP | 4-212373 A | 8/1992 | |
| JP | 2007-533371 A | 11/2007 | |
| JP | 2008081893 A * | 4/2008 | |
| JP | 2010-94962 A | 4/2010 | |
| JP | 2013-534462 A | 9/2013 | |
| WO | WO 2014/196651 A1 | 12/2014 | |
| WO | WO-2015121350 A1 * | 8/2015 | ............. A61L 15/28 |
| WO | WO 2016/047380 A1 | 3/2016 | |
| WO | WO 2016/117208 A1 | 7/2016 | |

OTHER PUBLICATIONS

Chakrabarty et al. Separation and Purification Technology 2010 75:174-182 (Year: 2010).*
Ma et al. International Journal of Molecular Science 2014 15:5426-5445 (Year: 2014).*
Talbott et al. Journal of Composite Materials 1987 21:1056-1081 (Year: 1987).*
Extended European Search Report dated Aug. 6, 2020, in European Patent Application No. 17882309.2.
Butkova et al., "Features of the Structural Characteristics of Filter Materials for Leukofiltration of Blood," Fibre Chemistry, vol. 43, No. 4, Nov. 15, 2011 (Russian Original No. 4, Jul.-Aug. 2011), pp. 275-279, XP035069843.
Extended European Search Report, dated Jul. 21, 2020, for European Application No. 17884518.6.
Sadrjahani et al., "Aligned Electrospun Sulfonated Poly(ether ether ketone) Nanofiber-Based Proton Exchange Membranes for Fuel Cell Applications." Polymer Engineering and Science, vol. 57, No. 8, 2017 (Sep. 26, 2016). pp. 789-796, XP055713872.
International Preliminary Report on Patentability and Written Opinion of the International Searching Authority dated Jul. 4, 2019, for International Application No. PCT/JP2017/046243.

(Continued)

*Primary Examiner* — Robert A Wax
*Assistant Examiner* — Caralynne E Helm
(74) *Attorney, Agent, or Firm* — Birch, Stewart, Kolasch & Birch, LLP

(57) ABSTRACT

Provided is a bone fixation material that does not deteriorate in properties even by an electron beam sterilization treatment performed before or during use as a bone fixation material, has fatigue resistance, wear resistance, and dimensional stability at excellent levels, also has biocompatibility, and offers excellent osteoconnectivity. The bone fixation material according to the present invention includes a nonwoven fabric made of PEEK fibers. The bone fixation material according to the present invention preferably has an average pore size of 3 to 280 μm and preferably has a porosity of 15% to 70%. The PEEK fibers preferably have an average fiber diameter of 10 μm or less.

10 Claims, 2 Drawing Sheets

(56) References Cited

OTHER PUBLICATIONS

International Search Report for International Application No. PCT/JP2017/046237 dated Mar. 6, 2018,
International Search Report, dated Mar. 6, 2018, for International Application No. PCT/JP2017/046243.
Jiya et al., "Posterior lumbar interbody fusion using non resorbable poly-ether-ether-ketone versus resorbable poly-L-lactide-co-D, L-lactide fusion devices. Clinical outcome at a minimum of 2-year follow-up", Eur Spine J. vol. 20, 2011, pp. 618-622 (5 pages).
Kido et al., "Surgical Results of Posterior Lumbar Interbody Fusion (PLIF) Using Peek Cage", Journal of the Eastern Japan Association of Orthopaedics and Traumatology, vol. 24, No. 3, 2012, pp. 329 (with english translation.).
Kiyota et al., "Clinical Results and Variation in X-Ray for 2Years After Anterior Cervical Fusion Using Peek Cage", Orthopedics & traumatology, vol. 64, No. 1, 2015, pp. 47-50 with an English translation.
Written Opinion of the International Searching Authority for International Application No. PCT/JP2017/046237, dated Mar. 6, 2018.
U.S. Office Action, dated Feb. 5, 2021, for U.S. Appl. No. 16/472,706.

\* cited by examiner

[FIG. 1]
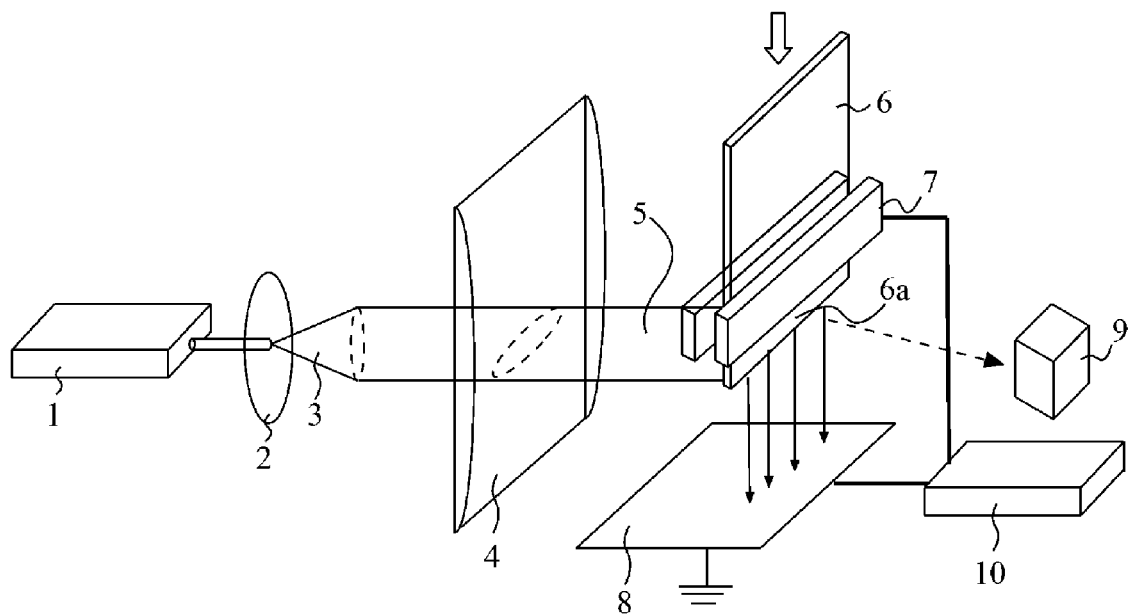
[FIG. 2]
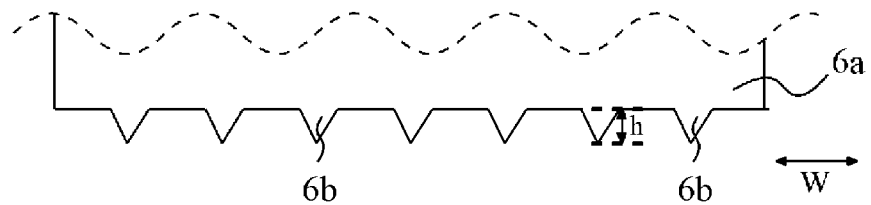

[FIG. 3]
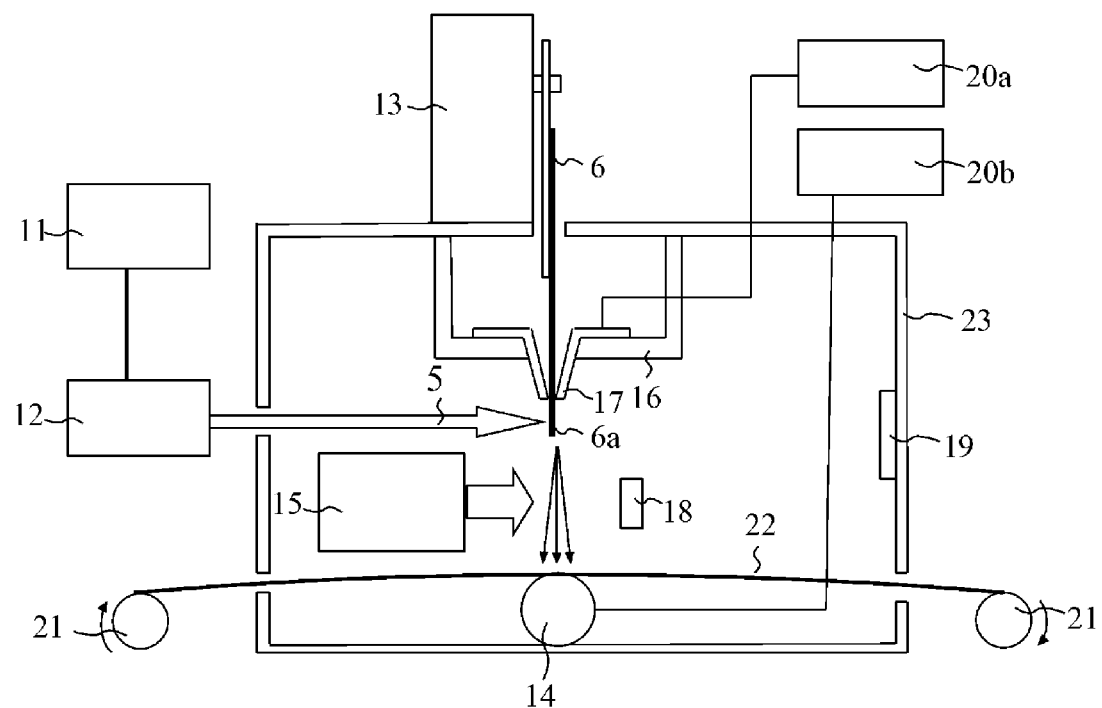
[FIG. 4]
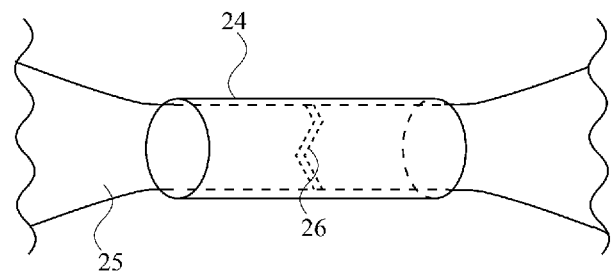
[FIG. 5]
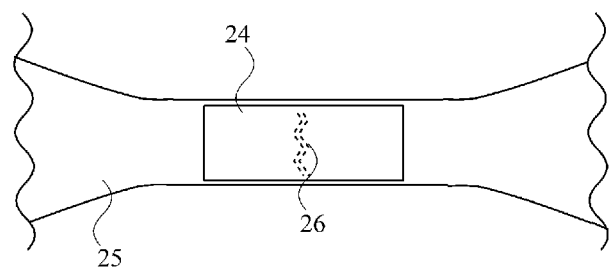

BONE FIXING MATERIAL

TECHNICAL FIELD

The present invention relates to bone fixing materials (bone fixation materials) for use in the medical field. This application claims priority to Japanese Patent Application No. 2016-249366, filed to Japan on Dec. 22, 2016, the entire contents of which are incorporated herein by reference.

BACKGROUND ART

Conventionally, in the medical field, bone fixation materials have been used for the purpose of repairing, reinforcing, and/or protecting injury areas typically in the bone tissue, where the injury has been caused typically by a disease or in an accident. The bone fixation materials are used by enveloping or covering such a bone injury area, or by enveloping or covering an artificial bone or by being incorporated into an artificial bone. Non-limiting examples of the artificial bone include non-resorbable materials (such as HAP), resorbable materials (such as β-TCP), and setting materials (such as α-TCP), which augment a bone injury portion. The bone fixation materials are implanted in, and remain in a living body without in-vivo decomposition and absorption and therefore require biological functions such as osteoconnectivity and biocompatibility. The bone fixation materials also require such durability as to resist deterioration over a long duration.

Conventionally used materials to form the bone fixation materials as above are resins such as polyacrylonitriles, poly(ether ketone)s, polyimides, aromatic polymers, and aliphatic polymers (PTL 1).

CITATION LIST

Patent Literature

PTL 1: Japanese Unexamined Patent Application Publication (JP-A) (Translation of PCT Application) No. 2007-533371

SUMMARY OF INVENTION

Technical Problem

The resins described in PTL 1, however, disadvantageously deteriorate in properties when subjected to electron beam sterilization treatment before or during use as bone fixation materials. In addition, these resins do not always have good biocompatibility.

Accordingly, the present invention has an object to provide a bone fixation material that does not deteriorate in properties even by electron beam sterilization treatment performed before or during use as a bone fixation material, has not only fatigue resistance, wear resistance, and dimensional stability at excellent levels, but also biocompatibility, and offers excellent osteoconnectivity.

Solution to Problem

After intensive investigations to achieve the object, the inventors of the present invention found that a bone fixation material that achieves the object can be prepared using a nonwoven fabric made of poly(ether ether ketone) (PEEK) fibers. The present invention has been made on the basis of these findings.

Specifically, the present invention provides a bone fixation material including a nonwoven fabric made of PEEK fibers.

The bone fixation material according to the present invention preferably has an average pore size of 3 to 280 µm.

The bone fixation material according to the present invention preferably has a porosity of 15% to 70%.

The PEEK fibers in the bone fixation material according to the present invention preferably have an average fiber diameter of 10 µm or less.

In the bone fixation material according to the present invention, the nonwoven fabric preferably has a mass per unit area of 10 to 100000 g/m$^2$.

In the bone fixation material according to the present invention, the nonwoven fabric preferably has a thickness of 0.05 to 100 mm.

The PEEK fibers in the bone fixation material according to the present invention preferably have a degree of crystallinity of 30% or less.

Advantageous Effects of Invention

The bone fixation material according to the present invention is made mainly of PEEK, thereby does not deteriorate in properties even by electron beam sterilization treatment performed before or during use as a bone fixation material, has fatigue resistance, wear resistance, and dimensional stability at excellent levels, offers dynamic characteristics similar to those of the bone, and also has biocompatibility. The bone fixation material according to the present invention includes PEEK fibers, or a nonwoven fabric made of PEEK fibers, thereby also has excellent osteoconnectivity, and readily adheres to the bone. This offers an expectation of early bone regeneration. The bone fixation material according to the present invention uses PEEK fibers, thereby is very flexible, and is free from fear of damage on bone or surrounding soft tissues. The bone fixation material according to the present invention uses PEEK fibers, thereby does not form sharp pieces, and lightly affects the human body. The bone fixation material has both strength and flexibility and thereby is capable of undergoing shape correction in situ in an operation. In addition, the bone fixation material according to the present invention is not absorbed into the body, and this can eliminate or minimize adhesion typically to the internal organs after operation.

BRIEF DESCRIPTION OF DRAWINGS

FIG. 1 is a schematic illustration of a PEEK fiber production method according to an embodiment;

FIG. 2 is a schematic view of Taylor cones formed in a band-like melt zone;

FIG. 3 is a schematic cross-sectional view of nonwoven fabric production equipment according to an embodiment, which employs or includes the PEEK fiber production method;

FIG. 4 schematically illustrates how to use the bone fixation material according to the present invention, in an embodiment where the bone fixation material is tubular; and FIG. 5 schematically illustrates how to use the bone fixation material according to the present invention, in an embodiment where the bone fixation material is sheet-like.

DESCRIPTION OF EMBODIMENTS

Bone Fixation Material

The bone fixation material according to the present invention serves as a bone reinforcer (bone protector). The bone fixation material characteristically includes PEEK fibers, or a nonwoven fabric made of PEEK fibers. The bone fixation material is in the form of, for example, a sheet or a tube (cylinder) and is a porous material having a multiplicity of pores. How to use the bone fixation material according to the present invention is illustrated in FIG. 4 in an embodiment where the material is tubular; and is illustrated in FIG. 5 in an embodiment where the material is sheet-like. It is also acceptable that a sheet-like bone fixation material is shaped into a tube (cylinder) before or during use. The bone fixation material according to the present invention is used typically as covering a bone lesion area.

The bone fixation material has an average pore size of typically 3 to 280 µm, preferably 5 to 260 µm, more preferably 10 to 240 µm, and furthermore preferably 20 to 220 µm. The bone fixation material, when having an average pore size within the range, allows neoplastic osteoblasts to readily enter and grow in the pores, to become readily integrable with the bone tissue, and to easily adhere to the bone. This offers an expectation of early bone regeneration. The average pore size can be measured typically by measuring sizes of pores as observed typically in an electron photomicrograph, and determining the average of the measured pore sizes.

The bone fixation material has a porosity (pore content) of typically 15% to 70%, preferably 20% to 65%, and more preferably 25% to 60%. The bone fixation material, when having a porosity within the range, allows neoplastic osteoblasts to readily enter and grow in the pores, to become readily integrable with the bone tissue, and to easily adhere to the bone. This offers an expectation of early bone regeneration. The porosity can be measured by determining the area of pores per unit area as observed using an electron photomicrograph.

The bone fixation material according to the present invention has a thickness of typically about 0.05 to about 100 mm, preferably 0.1 to 50 mm, more preferably 0.2 to 20 mm, and furthermore preferably 0.3 to 10 mm. The bone fixation material has a density of typically about 0.05 to about 1.2 $g/cm^3$, preferably 0.1 to 1.0 $g/cm^3$, and more preferably 0.2 to 0.8 $g/cm^3$. The bone fixation material according to the present invention may have any size as long as being such a size as to cover the bone lesion area. The bone fixation material, when being in the form of sheet, may have a length of one side of the sheet of typically 10 to 600 mm, and preferably 50 to 400 mm.

The bone fixation material according to the present invention is not particularly limited, as long as including a nonwoven fabric made of PEEK fibers. The content of the nonwoven fabric made of PEEK fibers is typically 50 weight percent or more, preferably 70 weight percent or more, more preferably 80 weight percent or more, and furthermore preferably 90 weight percent or more, of the totality of the bone fixation material. In addition to the nonwoven fabric made of PEEK fibers (PEEK fiber nonwoven fabric), the bone fixation material may further include any of other components such as other thermoplastic resins, thermosetting resins, metals, and ceramics, within such ranges as not to adversely affect the advantageous effects of the present invention.

The bone fixation material according to the present invention may be subjected to hydrophilization treatment for the purpose of surface modification. The hydrophilization treatment allows the bone fixation material to have a finer porous structure at its surface. Non-limiting examples of the hydrophilization treatment include plasma treatment, graft reaction after plasma treatment, corona discharge treatment, glow discharge treatment, alkaline solution treatment, acid solution treatment, oxidizer treatment, silane coupling treatment, anodizing treatment, and roughening treatment. Among them, plasma treatment, graft reaction after plasma treatment, and corona discharge treatment are typified.

The plasma treatment is performed typically by applying microwave plasma to the surface of the bone fixation material in the atmosphere (air) using a microwave plasma processor. Assume that the microwave plasma processor is a scanning-and-processing device in which a sample passes immediately below the plasma reactor at a uniform velocity. In this case, the travel speed (feed speed) of the sample is generally about 1 to about 20 m/min. Non-limiting examples of the (gas) plasma include oxygen, nitrogen, argon, and hydrogen. Instead of the air atmosphere, the plasma treatment may also be performed in another atmosphere such as nitrogen or argon atmosphere, or in a vacuum. A non-limiting example of the microwave plasma processor for use herein is a microwave plasma processor (microwave plasma system) supplied by Nissin Inc.

The graft reaction after plasma treatment is performed typically by immersing the bone fixation material after the plasma treatment in an acrylic acid substance such as methyl acrylate or ethyl acrylate in an atmosphere typically of nitrogen or argon for reaction with the acrylic acid substance. The graft reaction can further modify (hydrophilize) the surface of the porous shaped article. The acrylic acid substance for use herein may be a solution resulting from moderate dilution of the substance with an organic solvent such as toluene. The immersion is generally performed for about 1 to about 48 hours and may be performed at room temperature or at a temperature of about 30° C. to about 80° C.

The corona discharge treatment is performed typically by applying corona discharge electrons to the surface of the bone fixation material, where the electrons result from corona discharge in the atmosphere (air) using a corona discharge surface treatment system. When the corona discharge surface treatment system employs a conveyor system, the feed speed of the conveyor is generally about 1 to about 20 m/min, and the corona discharge is performed at an output of generally about 30 to about 500 W. A non-limiting example of the corona discharge surface treatment system for use herein is a corona discharge surface treatment system supplied by WEDGE Co., Ltd.

The bone fixation material according to the present invention may be subjected to $Ca^{2+}$ treatment by immersing the same in an aqueous solution typically of calcium hydroxide ($Ca(OH)_2$), calcium dihydrogenphosphate ($Ca(H_2PO_4)_2$), or calcium chloride ($CaCl_2$). The immersion may be performed for a duration of typically 1 to 30 days, and preferably 3 to 20 days. The $Ca^{2+}$ treatment allows the bone fixation material to more readily bear apatite formed on the surface thereof and to more readily have better osteoconductivity.

PEEK Fibers

The PEEK fibers are preferably fibers having small fiber diameters and may have diameters of typically 10 µm or less (0.1 to 10 µm). The PEEK fibers have diameters of preferably 0.5 to 8 µm, and more preferably 0.7 to 6 µm. The fibers having diameters as above may include fine fibers having fiber diameters of typically about 50 to about 1000 nm. The diameters of the PEEK fibers can be adjusted by appropriately adjusting conditions for the after-mentioned PEEK fiber production method, such as polymer sheet thickness, polymer sheet feed speed, and laser intensity. The diameters of the PEEK fibers can be measured typically using an electron microscope.

The PEEK fibers, when considered as an assembly, have an average fiber diameter (average diameter) of typically 10

μm or less (0.1 to 10 μm), preferably 0.5 to 8 μm, and more preferably 0.7 to 6 μm. The average fiber diameter can be determined typically by taking two or more (e.g., ten) images of shapes of fibers using a scanning electron microscope; measuring diameters of about ten fibers per image optionally selected from the images, typically using image processing software; and averaging the measured diameters.

The PEEK fibers have a degree of crystallinity of typically 30% or less, preferably 29% or less, and more preferably 28% or less. The PEEK fibers, when having a degree of crystallinity of 30% or less, offer excellent workability and can be readily shaped into a nonwoven fabric. The degree of crystallinity can be determined by a technique such as X-ray diffractometry, differential scanning calorimetry (using a differential scanning calorimeter; DSC), or densimetry. The degree of crystallinity is a value calculated from the amount of heat (calorie) determined by differential scanning calorimetry (DSC) by a method described in a working example.

The PEEK fibers include PEEK in a proportion of typically 50 weight percent or more, preferably 70 weight percent or more, more preferably 80 weight percent or more, and furthermore preferably 90 weight percent or more, of the totality of the PEEK fibers. Particularly preferably, the PEEK fibers are made of PEEK alone. The PEEK fibers may include any of other components such as other thermoplastic resins and additives, in addition to PEEK. The PEEK fibers are preferably prepared using the after-mentioned polymer sheet as a starting material, by the after-mentioned PEEK fiber production method.

Nonwoven Fabric

The nonwoven fabric is a sheet-like assembly of the PEEK fibers. The thickness of the nonwoven fabric may be selected within the range of typically about 0.05 to about 100 mm according to the intended purpose, but is preferably 0.1 to 50 mm, more preferably 0.2 to 20 mm, and furthermore preferably 0.3 to 10 mm. The nonwoven fabric has a mass per unit area (METSUKE) of typically about 10 to about 100000 $g/m^2$, preferably 20 to 20000 $g/m^2$, and more preferably 50 to 10000 $g/m^2$. The geometries or dimensions, such as fiber diameter, thickness, and mass per unit area, of the nonwoven fabric to be produced can be controlled by adjusting conditions such as sheet feed speed, laser intensity, as well as collection member traveling speed in the after-mentioned nonwoven fabric production method.

The nonwoven fabric may include the PEEK fibers in a content of typically 50 weight percent or more, preferably 70 weight percent or more, more preferably 80 weight percent or more, and furthermore preferably 90 weight percent or more, of the totality of the nonwoven fabric. The nonwoven fabric may further include other components in addition to the PEEK fibers, within ranges not adversely affecting the advantageous effects of the present invention. Non-limiting examples of the other components include other thermoplastic resins, thermosetting resins, metals, and ceramics.

Bone Fixation Material Production Method

The bone fixation material according to the present invention may be obtained typically, but non-limitingly, by producing PEEK fibers, and producing a nonwoven fabric from the PEEK fibers. Hereinafter, the PEEK fiber production method, and the PEEK fiber nonwoven fabric production method will be described.

PEEK Fiber Production Method

The PEEK fibers can be produced typically, but non-limitingly, by a laser melt electrospinning technique. Namely, the PEEK fibers may be, for example, laser melt electrospun PEEK fibers. According to the PEEK fiber production method, the PEEK fibers are produced in the following manner. Planar laser light (laser sheet) is applied to a polymer sheet to heat and melt an edge of the polymer sheet linearly to thereby form a band-like melt zone. With this, a potential difference is applied between the band-like melt zone and a fiber collector to form needle protrusions in the band-like melt zone of the polymer sheet and to allow fibers ejected from the needle protrusions to fly toward the fiber collector. The fibers are collected on the fiber collector or on a collection member disposed between the band-like melt zone and the fiber collector, to give the PEEK fibers.

The laser melt electrospinning technique will be illustrated with reference to the attached drawings. FIG. 1 is a schematic illustration of the PEEK fiber production method according to an embodiment.

In the PEEK fiber production method as illustrated in FIG. 1, laser light having a spot cross section emitted from a laser source 1 is converted into planar laser light 5 having a linear cross section, by the working of a light-path controller. The light-path controller includes a beam-expander-homogenizer 2, a collimation lens 3, and a cylindrical lens group 4. The planar laser light 5 is applied to an edge of a polymer sheet 6 held by a holder 7, to form a band-like melt zone 6a. With this, a voltage is applied from a high voltage generator 10 to form a potential difference between the band-like melt zone 6a and a fiber collector 8 disposed under the polymer sheet 6. A thermography 9 observes the temperature of the band-like melt zone 6a so as to optimize conditions such as the voltage and the laser light to be applied.

In the embodiment illustrated in FIG. 1, the holder 7, which holds the polymer sheet 6, functions also as an electrode and, when receives the voltage from the high voltage generator 10, imparts an electric charge to the band-like melt zone 6a of the polymer sheet 6, where the melt zone 6a is formed by the application of the planar laser light 5. The fiber collector 8 has a surface electric resistance approximately comparable to those of metals. The fiber collector 8 may have a shape selected typically from plate, roller, belt, net, sawlike, wave, needle, and linear shapes.

FIG. 2 is a schematic view of Taylor cones formed in the band-like melt zone 6a. As illustrated in FIG. 2, at the surface of the band-like melt zone 6a to which electric charges are applied, needle protrusions (Taylor cones) 6b are gradually formed due to building up and repelling of the electric charges on the surface. When the repulsive force of the electric charges exceeds the surface tension, the molten polymer sheet is ejected as fibers from the tips of the Taylor cones toward the fiber collector 8 by the action of electrostatic attraction. Namely, fibers are formed from the needle protrusions 6b and fly toward the fiber collector 8. As a result, the fibers elongate and are collected by the fiber collector 8. In an embodiment, a collection member is disposed on or over the fiber collector 8. In this embodiment, the fibers are collected on the collection member. Specifically, in the PEEK fiber production method, a member for collecting fibers may be the fiber collector itself, or not the fiber collector, but a collection member (collecting member) disposed on or over the fiber collector.

The number of the Taylor cones (spacing between Taylor cones) as illustrated in FIG. 2 can be controlled by changing the thickness of the polymer sheet 6 as appropriate. The "growth" of a Taylor cone refers to increase in height (h in FIG. 2) of the Taylor cone.

The number of the Taylor cones is not particularly limited, but preferably 1 to 100, more preferably 1 to 50, and furthermore preferably 2 to 10, per 2 cm in the width direction of the heated, melt zone of the polymer sheet.

When Taylor cones are present in a number of 1 to 100 per 2 cm in the width direction, the fibers can be surely produced in an appropriate production volume without decrease in fiber uniformity ratio caused typically by electric repulsion between the Taylor cones.

Non-limiting examples of the laser source include YAG laser, carbon dioxide gas ($CO_2$) laser, argon laser, excimer laser, and helium-cadmium laser. Among them, carbon dioxide gas laser is preferred because of having high power-supply efficiency and high capability of melting PEEK resins. The laser light may have a wavelength of preferably about 200 nm to about 20 μm, more preferably about 500 nm to about 18 μm, and furthermore preferably about 5 to about 15 μm.

The laser light, when to be applied as planar laser light in the PEEK fiber production method, preferably has a thickness (plane thickness) of about 0.5 to about 10 mm. The laser light, if having a thickness of less than 0.5 mm, may fail to invite the formation of Taylor cones. The laser light, if having a thickness of greater than 10 mm, may cause deterioration of the material because of longer residence time during melting.

The power (output) of the laser light may be controlled within such a range that the band-like melt zone has a temperature equal to or higher than the melting point of the polymer sheet and equal to or lower than the ignition point of the polymer sheet. The power is preferably high from the viewpoint of allowing the ejected PEEK fibers to have small fiber diameters. The specific power of the laser light can be selected as appropriate according typically to properties (such as melting point and limiting oxygen index (LOI)) and shape of the polymer sheet to be used, and to the feed speed of the polymer sheet. The power is preferably about 5 to about 100 W per 13 cm, more preferably 20 to 60 W per 13 cm, and furthermore preferably 30 to 50 W per 13 cm. The power of the laser light is the power (output) of an outgoing spot beam from the laser source.

The temperature of the band-like melt zone is not particularly limited, as long as being equal to or higher than the melting point (334° C.) of PEEK and equal to or lower than the ignition point of PEEK, but is generally about 350° C. to about 600° C., and preferably 380° C. to 500° C.

In the PEEK fiber production method illustrated in FIG. 1, the laser light is applied from only one direction to the band-like melt zone (edge) of the polymer sheet. In another embodiment, the laser light may be applied typically from two directions with a reflective mirror to the band-like melt zone (edge) of the polymer sheet. This configuration contributes to more uniform melting of the edge of the polymer sheet even when the polymer sheet has a large thickness.

In the PEEK fiber production method, the potential difference to be generated between the edge of the polymer sheet and the collection member is preferably such a potential difference as to give a high voltage within a range not causing discharge. The potential difference can be selected as appropriate according typically to the required fiber diameter, the distance between the electrode and the collection member, and the irradiance of the laser light, and is generally about 0.1 to about 30 kV/cm, preferably 0.5 to 20 kV/cm, and more preferably 1 to 10 kV/cm.

The voltage may be applied to the melt zone of the polymer sheet by a direct application technique, in which the portion to be irradiated with the laser light (band-like melt zone of the polymer sheet) is coincident with an electrode unit for imparting the electric charges. However, the voltage is preferably applied by an indirect application technique, in which the portion to be irradiated with the laser light is disposed at a position different from the position of the electrode unit for imparting the electric charges. The indirect application technique is preferred because equipment for this technique can be prepared easily and simply, the laser light can be effectively converted into thermal energy, and the reflection direction of the laser light can be easily controlled to offer high safety. Among such indirect application techniques, preferred is a technique in which the portion to be irradiated with the laser light is disposed downstream from the electrode unit in the feeding direction of the polymer sheet. In particular, in a preferred embodiment of the production method, the planar laser light is applied to the polymer sheet downstream from the electrode unit, and the distance between the electrode unit and the portion to be irradiated with the laser light (e.g., the distance between the lower end of the electrode unit and the upper outer periphery of the planar laser light) is controlled within a specific range (e.g., about 10 mm or less). This distance can be selected according typically to the electric conductivity, thermal conductivity, and glass transition point of the polymer sheet, and the irradiance of the laser light. The distance is preferably about 0.5 to about 10 mm, more preferably about 1 to about 8 mm, furthermore preferably about 1.5 to about 7 mm, and particularly preferably about 2 to about 5 mm. When the two portions are disposed at a distance within the range, the resin adjacent to the portion to be irradiated with the laser light offers higher molecular mobility and can receive sufficient electric charges in a molten state. This contributes to better productivity.

The distance between the edge of the polymer sheet (tip of a Taylor cone) and the collection member is not limited and may be generally 5 mm or more. For efficient production of fibers having small diameters, the distance is preferably 10 to 300 mm, more preferably 15 to 200 mm, furthermore preferably 50 to 150 mm, and particularly preferably 80 to 120 mm.

The polymer sheet, when fed continuously, is fed at a feed speed of preferably about 2 to about 20 mm/min, more preferably 3 to 15 mm/min, and furthermore preferably 4 to 10 mm/min. The feeding of the polymer sheet at a higher speed contributes to higher productivity. However, the feeding, if performed at an excessively high speed, may impede fiber productivity due to insufficient melting of the polymer sheet in the portion irradiated with the laser light. In contrast, the feeding, if performed at an excessively low speed, may cause decomposition of the polymer sheet and/or may invite lower productivity.

The polymer sheet has a degree of crystallinity of preferably 25% or less, more preferably 20% or less, and furthermore preferably 15% or less. The polymer sheet, when having a degree of crystallinity of 25% or less, can give PEEK fibers having a low degree of crystallinity. The degree of crystallinity of the polymer sheet can be determined by a technique similar to that for the degree of crystallinity of the PEEK fibers.

The polymer sheet preferably has a low melt viscosity so as to readily give fibers having small fiber diameters. The melt viscosity of the polymer sheet is preferably 800 Pa·s or less (50 to 800 Pa·s), more preferably 600 Pa·s or less, and furthermore preferably 400 Pa·s or less, where the melt viscosity is measured at 400° C. and a shear rate (shearing velocity) of 121.6 $s^{-1}$. The melt viscosity can be determined by the method described in the working example, using a capillary rheometer Capillograph 1D (trade name, supplied by Toyo Seiki Seisaku-Sho, Ltd.). The shear rate can also be measured using such a capillary rheometer.

The polymer sheet can be produced typically by heating, melting, and shaping PEEK in the form of chips into a sheet using a device such as a T-die extruder. The PEEK chips may be available as commercial products, of which one under the trade name of VESTAKEEP 1000G (supplied by Daicel-Evonik Ltd.), for example, is advantageously usable. The heating temperature of the T-die extruder has only to be equal to or higher than the melting point of PEEK and is typically 350° C. to 400° C.

The polymer sheet may contain any of various additives for use in fibers. Non-limiting examples of the additives include infrared absorbents, stabilizers (such as antioxidants, ultraviolet absorbers, and thermal stabilizers), flame retardants, antistatic agents, colorants, fillers, lubricants, antibacterial agents, insect/tick repellents, antifungal agents, flatting agents, heat storage media, flavors, fluorescent brighteners, wetting agents, plasticizers, thickeners, dispersants, blowing agents, and surfactants. The polymer sheet may contain each of different additives alone or in combination.

Among these additives, a surfactant is preferably used. Assume that a high voltage is applied to the polymer sheet to inject electric charges into the polymer sheet. In this case, the polymer sheet offers high electric insulation and it therefore is difficult to inject the electric charges into a thermally melt zone having a lower electric resistance. However, the use of a surfactant allows the polymer sheet having high electric insulation to have lower electric resistance in its surface, and this allows the electric charges to be injected sufficiently into the thermally melt zone. Compounding of an additive such as a surfactant is effective for phase separation of multiple components contained in the polymer sheet upon application of a high voltage to the polymer sheet to inject electric charges into the sheet.

The polymer sheet may contain any of these additives each in a proportion of 50 parts by weight or less, preferably 0.01 to 30 parts by weight, and more preferably 0.1 to 5 parts by weight, per 100 parts by weight of the resin constituting the polymer sheet.

The polymer sheet has a thickness of preferably 0.01 to 10 mm, and more preferably 0.05 to 5.0 mm. The polymer sheet, when having a thickness within the range, contributes to easy production of the PEEK fibers.

In the PEEK fiber production method, space between the edge of the polymer sheet and the collection member may be in an inert gas atmosphere. The presence of the inert gas atmosphere in the space restrains the ignition of the fibers and allows the laser light to be applied at a higher power. Non-limiting examples of the inert gas include nitrogen gas, helium gas, argon gas, and carbon dioxide gas. Among them, nitrogen gas is generally used. In addition, the use of the inert gas can restrain oxidation reactions in the band-like melt zone.

The space may be heated. The heating allows the resulting fibers to have smaller diameters. Specifically, heating of the air or inert gas in the space can restrain abrupt temperature fall of fibers under growing, and this promotes growth or extension of the fibers to give more ultrafine fibers. The heating may be performed typically by using a heater (such as a halogen heater) or by applying laser light. The heating temperature may be selected typically within the range of from 50° C. to lower than the ignition point of the resin. In consideration of spinnability, the heating temperature is preferably lower than the melting point of PEEK.

PEEK Fiber Nonwoven Fabric Production Method

Next, a method for producing a PEEK fiber nonwoven fabric (PEEK fiber nonwoven fabric production method) according to an embodiment will be illustrated. By the below-mentioned PEEK fiber nonwoven fabric production method a nonwoven fabric is obtained by continuously performing the above-mentioned PEEK fiber production method while moving, with time, the position at which the fibers are collected, and collecting and accumulating the fibers to form a sheet, where the fibers have flown toward the fiber collector. The nonwoven fabric made of PEEK fibers (PEEK fiber nonwoven fabric) may be produced by the method described below, or by preparing PEEK fibers by the above-mentioned PEEK fiber production method and forming the PEEK fibers into a nonwoven fabric by another technique.

Exemplary techniques for moving with time the position at which the fibers flown toward the fiber collector are collected include (1) the technique of moving the collection member (or the fiber collector when the fiber collector itself functions as a collection member); (2) the technique of moving the position at which the polymer sheet is held; (3) the technique of allowing mechanical, magnetic, or electric force to act upon fibers flying from the Taylor cones toward the collection member, such as the technique of blowing air to the fibers during flying; and (4) a technique as any selective combination of the techniques (1) to (3).

Among them, the technique (1), namely, the technique of moving the collection member is desirable, because this technique allows easy simplification of the configuration of the equipment and allows easy control of the geometries (such as thickness and mass per unit area) of the nonwoven fabric to be produced. The PEEK fiber nonwoven fabric production method will be illustrated in detail below, by taking a procedure using the technique (1) as an example.

The PEEK fiber nonwoven fabric production method using the technique (1) may be performed in the following manner. In the PEEK fiber production method illustrated in FIG. 1, a collection member is placed on the fiber collector 8; and, while moving the collection member in a direction (right hand or left hand in the figure) perpendicular to the width direction of the polymer sheet 6, the PEEK fiber production method is performed continuously. The collection member may be moved at a constant speed, or at a speed varying with time, or may be moved and stopped repeatedly. To continuously perform the PEEK fiber production method, the polymer sheet 6 may be continuously fed toward the fiber collector 8 (toward the collection member) with the progress of the fiber production process, as has been described above. The speed (feed speed) of the polymer sheet during the continuous feeding is as described in the PEEK fiber production method.

The moving speed of the collection member on or over the fiber collector 8 is not limited, may be selected as appropriate in consideration typically of the mass per unit area of the fiber sheet to be produced, and is generally about 10 to about 2000 mm/min. For example, assume that a polymer sheet having a mass per unit area of 1000 g/m$^2$ is fed at a feed speed of 0.5 mm/min. In this case, a nonwoven fabric having a mass per unit area of about 0.5 g/m$^2$ can be continuously produced by setting the moving speed of the collection member at about 1000 mm/min.

FIG. 3 is a schematic cross-sectional view of exemplary nonwoven fabric production equipment employing or including the PEEK fiber production method illustrated in FIG. 1. The equipment (nonwoven fabric production equipment) illustrated in FIG. 3 includes a laser source 11; a light-path controller 12; a polymer sheet feeder 13 capable of continuously feeding the polymer sheet 6; and a cabinet 23. The cabinet 23 houses a holder 16 that holds the polymer sheet 6; an electrode 17 that applies electric charges to the polymer sheet 6; a collection member 22 that collects fibers; a fiber collector 14 that is disposed so as to face the electrode 17 through a band-like melt zone (edge) 6a of the polymer sheet 6 and the collection member 22; and a heating device 15. The equipment also includes high voltage generators 20a and 20b which apply a voltage respectively to the electrode 17 and to the fiber collector 14; and pulleys 21 for moving the collection member 22. The light-path controller 12 is an assembly of optical components as described above and includes, for example, the beam-expander-homogenizer 2, the collimation lens 3, and the cylindrical lens group 4 as illustrated in FIG. 1.

With reference to FIG. 3, the planar laser light 5, which is emitted from the laser source 11 and travels via the light-path controller 12, is introduced into the cabinet 23 and is applied to the band-like melt zone (edge) 6a of the polymer sheet 6. The polymer sheet feeder 13 is mounted on the upper side of the cabinet 23 and includes a motor, and a mechanism that converts the rotation of the motor into a rectilinear motion. The polymer sheet feeder 13 receives the polymer sheet 6 and continuously feeds the same into the cabinet 23. The lower part of the polymer sheet 6 is held by the holder 16 on which the electrode 17 is mounted. The polymer sheet 6 and the electrode 17 are always in contact with each other, and thus electric charges are applied to the polymer sheet 6 upon application of a voltage to the electrode 17.

The fiber collector 14, which functions as a counter electrode to the electrode 17, is disposed at such a position as to face the electrode 17 through the band-like melt zone (edge) 6a of the polymer sheet 6 and the collection member 22. This configuration gives a potential difference between the band-like melt zone (edge) 6a of the polymer sheet 6 and the collection member 22 when a voltage is applied between the electrode 17 and the fiber collector 14. The high voltage generators 20a and 20b are coupled respectively to the electrode 17 and to the fiber collector 14 and apply a voltage between the electrode 17 and the fiber collector 14. In the nonwoven fabric production equipment, the electrode 17 serves as a positive electrode, and the fiber collector 14 serves as a negative electrode. The reverse configuration will also do. The collection member 22 herein is a belt conveyor including the pulleys 21 and a conveyor belt, and the conveyor belt itself corresponds to the collection member 22. Accordingly, the collection member 22 (conveyor belt) travels to a predetermined direction (e.g., right hand in the figure) with the driving of the pulleys 21.

The nonwoven fabric production equipment illustrated in FIG. 3 includes the heating device 15 and can heat and keep warmth of fibers ejected and elongated from the band-like melt zone (edge) 6a of the polymer sheet 6 toward the collection member 22. The equipment also includes a laser light absorber 19 and a heat absorber 18 in the cabinet 23.

Using the nonwoven fabric production equipment illustrated in FIG. 3, a nonwoven fabric is produced in the following manner. While a voltage is applied between the electrode 17 and the fiber collector 14 and while the polymer sheet 6 is fed by the working of the polymer sheet feeder 13 and the holder 16, the planar laser light 5 is applied to the band-like melt zone (edge) 6a of the polymer sheet 6. This allows Taylor cones to form in the band-like melt zone (edge) 6a of the polymer sheet 6, allows the formed Taylor cones to eject fibers, and allows the fibers to fly (to be jetted) toward the fiber collector 14. As a result, elongated fibers are collected by the collection member 22, as has been described above. Then, while the polymer sheet 6 is continuously fed (while fibers are continuously ejected), the collection member 22 is moved, to give the nonwoven fabric on the collection member 22.

The collection member 22 in the nonwoven fabric production equipment illustrated in FIG. 3 is a sheet-like member. In this equipment, the collection member 22 is not limited, as long as being in the form of sheet, but may be made of a material selected typically from paper, films, various woven fabrics, nonwoven fabrics, and meshes. The collection member may also be a sheet or belt made of a metal or a material having a surface electric resistance comparable to those of metals.

In the nonwoven fabric production equipment illustrated in FIG. 3, materials to constitute the electrode 17 and the fiber collector 14 have only to be conductive materials (generally, metal components). Non-limiting examples of such materials include elementary metals typically of Group 6 elements such as chromium; Group 10 elements such as platinum; Group 11 elements such as copper and silver; Group 12 elements such as zinc; and Group 13 elements such as aluminum. The examples also include alloys of these metals (such as aluminum alloys and stainless alloys (stainless steels)), and compounds including these metals (exemplified by metal oxides such as silver oxide and aluminum oxide). The materials may include each of different metal components alone or in combination. Among the metal components, particularly preferred examples are copper, silver, aluminum, and stainless steels. The shape of the fiber collector 14 is exemplified by, but not limited to, plate, roller, belt, net, sawlike, wave, needle, and linear shapes. Among these shapes, plate and roller shapes are particularly preferred. Non-limiting examples of the laser light absorber 19 include metals and porous ceramics each coated with a black body. Non-limiting examples of the heat absorber 18 include black ceramics. The use of the equipment as described above enables efficient production of the nonwoven fabric.

The bone fixation material according to the present invention may be not only one produced by the above-mentioned production method, but also one produced through a press process in which a PEEK fiber nonwoven fabric is compression-molded as needed typically using a mold. The bone fixation material may also be an integrated assembly of multiple plies of the nonwoven fabric as stacked and compression-molded (pressed).

EXAMPLES

The present invention will be illustrated in further detail with reference to several examples below. It should be noted, however, that the examples are by no means intended to limit the scope of the present invention.

Example 1

Polymer Sheet Preparation

A polymer sheet having a thickness of 0.1 mm was prepared in the following manner. Sample chips of a PEEK, VESTAKEEP 1000G (trade name, supplied by Daicel-Evonik Ltd.) were extruded into a sheet using the LABO PLASTOMILL T-Die Extruder (supplied by Toyo Seiki Seisaku-Sho, Ltd.) with a T-die having a die width of 150 mm and a lip width of 0.4 mm, at an extrusion temperature of 345° C. to 360° C. The extruded sheet was coiled at a haul-off roller temperature of 140° C. and a coiling speed of 1.0 to 2.0 m/min to yield the polymer sheet.

The prepared polymer sheet had a melt viscosity (400° C.) of 151 Pa·s and a degree of crystallinity of 12.7%, where the melt viscosity was measured by a method mentioned below. The degree of crystallinity of the polymer sheet was determined by a method mentioned below for determining the degree of crystallinity of PEEK fibers constituting the nonwoven fabric.

Polymer Sheet Melt Viscosity (400° C.) Measurement Method

The melt viscosity of the polymer sheet was measured at 400° C. and a shear rate of 121.6 s$^{-1}$, using a capillary rheometer, Capillograph 1D (trade name, supplied by Toyo Seiki Seisaku-Sho, Ltd.) with a jig having a capillary diameter of 1 mm and a length of 10 mm.

Next, using the polymer sheet prepared by the above method, a PEEK fiber nonwoven fabric was produced by the following procedure.

PEEK Fiber Nonwoven Fabric Production

The PEEK fiber nonwoven fabric was produced using the nonwoven fabric production equipment schematically illustrated in FIG. 3.

The laser source 11 of the equipment illustrated in FIG. 3 used herein was a $CO_2$ laser system (supplied by Universal Laser Systems, Inc., having a wavelength of 10.6 μm and a power of 45 W, with air cooling, and having a beam diameter of 4 mm). The light-path controller 12 of the equipment illustrated in FIG. 3 used herein was one including a beam expander with 2.5-fold magnification, a homogenizer (having an incident beam diameter of 12 mm (designed value) and an outgoing beam diameter of 12 mm (designed value)), a collimation lens (having an incident beam diameter of 12 mm (designed value) and an outgoing beam diameter of 12 mm (designed value)), a cylindrical lens (plano-concave lens, f-30 mm), and another cylindrical lens (plano-convex lens, f-300 mm) disposed in the specified sequence at predetermined positions. By passing through these light-path controllers, the spot-like laser light was converted into planar laser light 5 having a width of about 150 mm and a thickness of about 1.4 mm and was applied to the band-like melt zone (edge) 6a of the polymer sheet 6. In this process, the laser light was emitted at an output of 61 W/13 cm, the polymer sheet was fed at a feed speed of 6 mm/min, and the potential difference between the electrode 17 and the fiber collector 14 was 6 kV/cm.

This gave a nonwoven fabric made of PEEK fibers having an average fiber diameter of 0.7 μm. The PEEK fibers constituting the nonwoven fabric had a degree of crystallinity of 24.0%, as measured by a measurement method mentioned below.

The produced nonwoven fabric was used as a bone fixation material. The bone fixation material had an average pore size of 200 μm and a porosity of 60%.

Method for Measuring Degree of Crystallinity of PEEK Fibers Constituting Nonwoven Fabric The degree of crystallinity of the PEEK fibers constituting the nonwoven fabric was calculated from the amount of heat determined by differential scanning calorimetry.

The differential scanning calorimetry (DSC) was performed using a differential scanning calorimeter DSC Q2000 (supplied by TA) with alumina as a reference material in a nitrogen atmosphere at temperatures in the range of 0° C. to 420° C. and a rate of temperature rise of 20° C./min.

On the basis of the amount of heat determined by the differential scanning calorimetry, the degree of crystallinity was determined according to the expression:

Degree of crystallinity (%)=[(Heat of fusion (J/g) of sample)−(Heat of recrystallization (J/g) of sample)]/(Heat of fusion of perfect crystal (130 (J/g))×100

Bone Fixation Material Average Pore Size Measurement

The bone fixation material according to Example 1 was cut to give a cross-section, arbitrary 30 or more pores viewed in an electron photomicrograph of the cross-section were selected, the areas of the selected pores were measured, and the average thereof was defined as the average pore area $S_{ave}$. Assuming that the pores are prefect circles, the average pore area was converted into a pore size (pore diameter) according to the following equation, and the converted value was defined as the average pore size. In the equation, π represents the ratio of the circumference of a circle to its diameter.

Average pore size (μm)=2×$(S_{ave}/π)^{1/2}$

Bone Fixation Material Porosity Measurement

The porosity of the bone fixation material according to Example 1 was calculated according to the following equation.

The volume and the weight of part or all (entire) of the bone fixation material were measured, where the portion had been cut from the bone fixation material.

In the following equation, V represents the volume (cm$^3$) of the bone fixation material; W represents the weight (g) of the bone fixation material; and ρ represents the density (g/cm$^3$) (the density of PEEK is 1.27):

Porosity [%]=100−100×W/(ρV)

REFERENCE SIGNS LIST 1 laser source
2 beam-expander-homogenizer
3 collimation lens
4 cylindrical lens group
5 planar laser light
6 polymer sheet
6a band-like melt zone
6b needle protrusion
7 holder
8 fiber collector
9 thermography
10 high voltage generator
11 laser source
12 light-path controller
13 polymer sheet feeder
14 fiber collector
15 heating device
16 holder
17 electrode
18 heat absorber
19 laser light absorber
20a high voltage generator
20b high voltage generator
21 pulley
22 collection member
23 cabinet
h height of Taylor cone
w width direction
24 bone fixation material
25 bone
26 bone lesion area As a summary of the above description, the configurations according to embodiments of the present invention, as well as variations thereof, will be listed below as appendices.

(1) A bone fixation material including a nonwoven fabric made of PEEK fibers.

(2) The bone fixation material according to (1), wherein the bone fixation material has an average pore size of 3 to 280 μm.

(3) The bone fixation material according to one of (1) and (2), wherein the bone fixation material has a porosity of 15% to 70%.

(4) The bone fixation material according to any one of (1) to (3), wherein the PEEK fibers have an average fiber diameter of 10 μm or less.

(5) The bone fixation material according to any one of (1) to (4), wherein the nonwoven fabric has a mass per unit area of 10 to 100000 g/m².

(6) The bone fixation material according to any one of (1) to (5), wherein the nonwoven fabric has a thickness of 0.05 to 100 mm.

(7) The bone fixation material according to any one of (1) to (6), wherein the PEEK fibers have a degree of crystallinity of 30% or less.

(8) The bone fixation material according to any one of (1) to (7), wherein the bone fixation material has a thickness of 0.05 to 100 mm.

(9) The bone fixation material according to any one of (1) to (8), which is in the form of sheet or tube.

(10) The bone fixation material according to any one of (1) to (9), wherein the bone fixation material has undergone hydrophilization treatment (such as plasma treatment, graft reaction treatment after plasma treatment, corona discharge treatment, glow discharge treatment, alkaline solution treatment, acid solution treatment, oxidizer treatment, silane coupling treatment, anodizing treatment, or roughening treatment).

(11) The bone fixation material according to any one of (1) to (10), wherein the PEEK fibers include PEEK in a proportion of 50 weight percent or more.

(12) The bone fixation material according to any one of (1) to (11), wherein the bone fixation material has a density of 0.05 to 1.2 g/cm³.

INDUSTRIAL APPLICABILITY

The bone fixation material according to the present invention is usable in the medical field so as to repair, reinforce, and/or protect an injury area typically of bone tissue, where the injury has been caused typically by a disease or in an accident.

The invention claimed is:

1. A method for fixing a bone comprising
covering a bone lesion area with a nonwoven fabric made of poly(ether ether ketone) (PEEK) fibers,
wherein the PEEK fibers have an average fiber diameter of 0.5 to 8 μm,
a bone fixation material comprising the nonwoven fabric has an average pore size of 3 to 280 μm,
the nonwoven fabric has a mass per unit area of 10 to 100,000 g/m², and
the PEEK fibers have a degree of crystallinity of 30% or less.

2. The method according to claim 1, wherein the bone fixation material comprising the nonwoven fabric has a porosity of 15% to 70%.

3. The method according to claim 1,
wherein the PEEK fibers have an average fiber diameter of 0.5 to 6 μm.

4. The method according to claim 1,
wherein the nonwoven fabric has a thickness of 0.05 to 100 mm.

5. The method according to claim 1,
wherein the nonwoven fabric has a thickness of 0.05 to 100 mm.

6. The method of claim 1, wherein said fabric is in the form of a sheet or a tube.

7. A method for producing a bone fixation material comprising
forming a nonwoven fabric made of poly(ether ether ketone) (PEEK) fibers,
wherein the PEEK fibers have an average fiber diameter of 0.5 to 8 μm,
the bone fixation material has an average pore size of 3 to 280 μm,
the nonwoven fabric has a mass per unit area of 10 to 100,000 g/m², and
the PEEK fibers have a degree of crystallinity of 30% or less.

8. The method according to claim 7,
wherein the bone fixation material has a porosity of 15% to 70%.

9. The method according to claim 7,
wherein the PEEK fibers have an average fiber diameter of 0.5 to 6 μm.

10. The method of claim 7, wherein said fabric is in the form of a sheet or a tube.

\* \* \* \* \*